United States Patent [19]
Ogle, II

[11] Patent Number: 5,456,668
[45] Date of Patent: Oct. 10, 1995

[54] RETRACTABLE VENIPUNCTURE CATHETER NEEDLE AND RECEPTACLE

[75] Inventor: George B. Ogle, II, Alta Loma, Calif.

[73] Assignee: F. H. Faulding & Co. Limited, South Australia, Australia

[21] Appl. No.: 181,901

[22] Filed: Jan. 14, 1994

[51] Int. Cl.[6] ................................................. A61M 3/00
[52] U.S. Cl. ........................... 604/110; 604/195; 604/240
[58] Field of Search ................................... 604/195, 110, 604/263, 194

[56] References Cited

U.S. PATENT DOCUMENTS

| | | |
|---|---|---|
| 3,463,152 | 6/1966 | Sorenson . |
| 3,536,073 | 10/1970 | Farb . |
| 4,108,175 | 8/1978 | Orton . |
| 4,160,450 | 7/1979 | Doherty . |
| 4,377,165 | 3/1983 | Luther et al. . |
| 4,425,120 | 1/1984 | Sampson et al. . |
| 4,475,905 | 10/1984 | Himmelstrup . |
| 4,500,312 | 2/1985 | McFarlane . |
| 4,573,976 | 3/1986 | Sampson et al. . |
| 4,588,398 | 5/1986 | Daugherty et al. . |
| 4,631,057 | 12/1986 | Mitchell . |
| 4,631,199 | 2/1987 | Jennings, Jr. et al. . |
| 4,643,200 | 2/1987 | Jennings, Jr. . |
| 4,664,653 | 5/1987 | Sagstetter et al. . |
| 4,664,654 | 5/1987 | Strauss . |
| 4,676,783 | 6/1987 | Jagger et al. . |
| 4,702,738 | 10/1987 | Spencer . |
| 4,723,943 | 2/1988 | Spencer . |
| 4,747,831 | 5/1988 | Kulli . |
| 4,762,516 | 8/1988 | Luther et al. . |
| 4,772,272 | 9/1988 | McFarland . |
| 4,781,692 | 11/1988 | Jagger et al. . |
| 4,790,827 | 12/1988 | Haber et al. . |
| 4,801,295 | 1/1989 | Spencer . |
| 4,828,549 | 5/1989 | Kvalo . |
| 4,832,696 | 5/1989 | Luther et al. . |
| 4,846,808 | 7/1989 | Haber et al. . |
| 4,892,107 | 1/1990 | Haber . |
| 4,900,310 | 2/1990 | Ogle, II . |
| 4,909,793 | 3/1990 | Vining et al. . |
| 4,950,252 | 8/1990 | Luther et al. . |
| 5,065,783 | 11/1991 | Ogle, II . |
| 5,067,490 | 11/1991 | Haber . |
| 5,069,341 | 12/1991 | Barbieri et al. . |
| 5,102,394 | 4/1992 | Lasaitis et al. . |
| 5,104,385 | 4/1992 | Huband . |
| 5,106,379 | 4/1992 | Leap . |
| 5,129,884 | 7/1992 | Dysarz . |
| 5,176,650 | 1/1993 | Haining . |
| 5,205,827 | 4/1993 | Novacek et al. . |
| 5,205,829 | 4/1993 | Lituchy . |
| 5,219,339 | 6/1993 | Saito . |
| 5,222,947 | 6/1993 | D'Amico . |
| 5,232,458 | 8/1993 | Chen . |
| 5,242,400 | 9/1993 | Blake, III et al. . |
| 5,256,152 | 10/1993 | Marks . |
| 5,273,540 | 12/1993 | Luther et al. . |
| 5,279,590 | 1/1994 | Sinko et al. . |
| 5,312,367 | 5/1994 | Nathan . |
| 5,312,368 | 5/1994 | Haynes . |

FOREIGN PATENT DOCUMENTS

| | | |
|---|---|---|
| 0023580 | 2/1981 | European Pat. Off. . |
| 0139872 | 5/1985 | European Pat. Off. . |

Primary Examiner—Corrine M. Maglione
Assistant Examiner—Perry E. Van Over
Attorney, Agent, or Firm—Christie, Parker & Hale

[57] ABSTRACT

Intravenous catheter apparatus includes a housing surrounding a carrier movable from a first to a second position. An elongated needle, secured at one end to the carrier, extends from the carrier through an opening in the housing so the other end of the needle with a sharp point extends away from the housing when the carrier is in the first position. Means are provided for moving with one hand the carrier from the first to the second position to retract the needle into the housing until the sharp end of the needle clears the opening and moves into the housing. Means deflect the needle laterally when the needle clears the opening so the needle moves out of alignment with the opening to prevent the needle from being moved back into the opening. Preferably, the housing is formed of two elongated, substantially symmetrical halves secured together at one end by a living hinge for ease of manufacture and assembly.

13 Claims, 4 Drawing Sheets

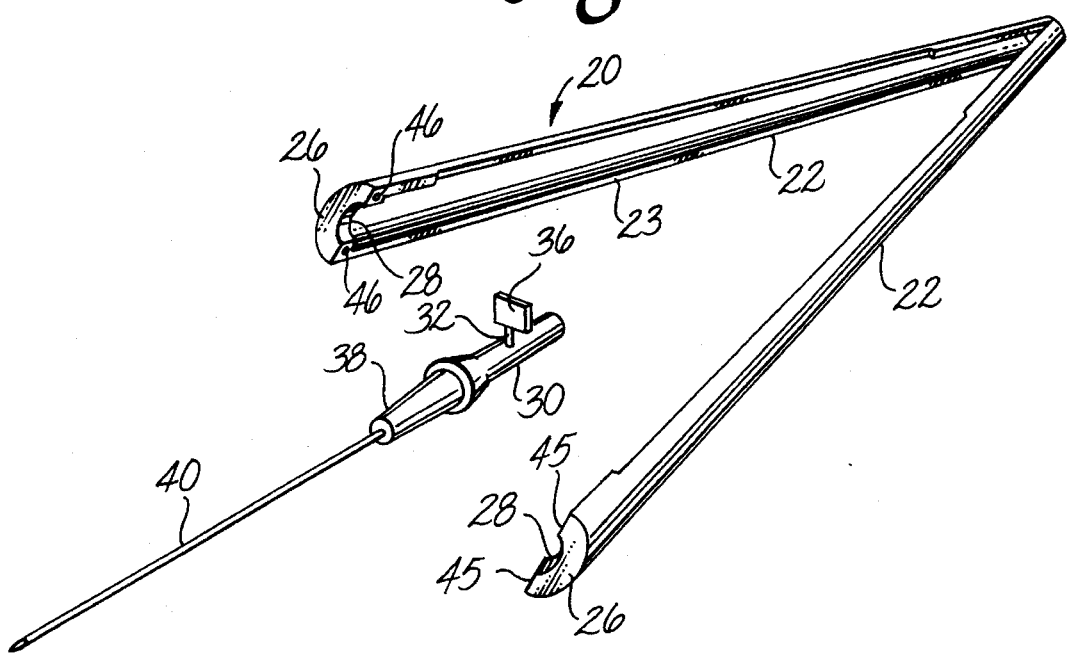
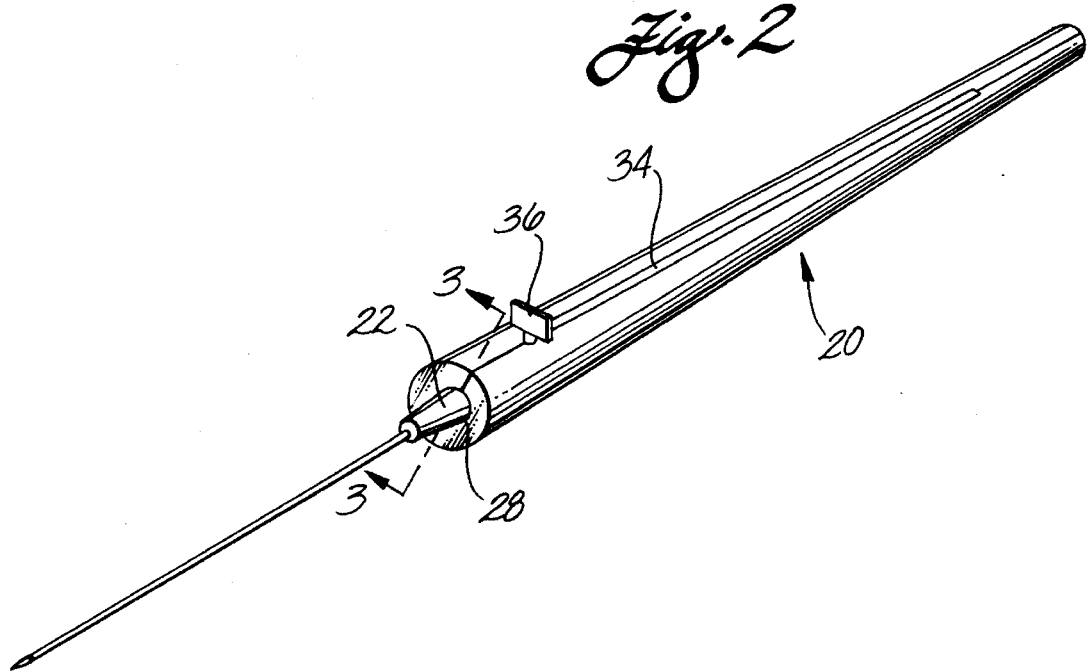

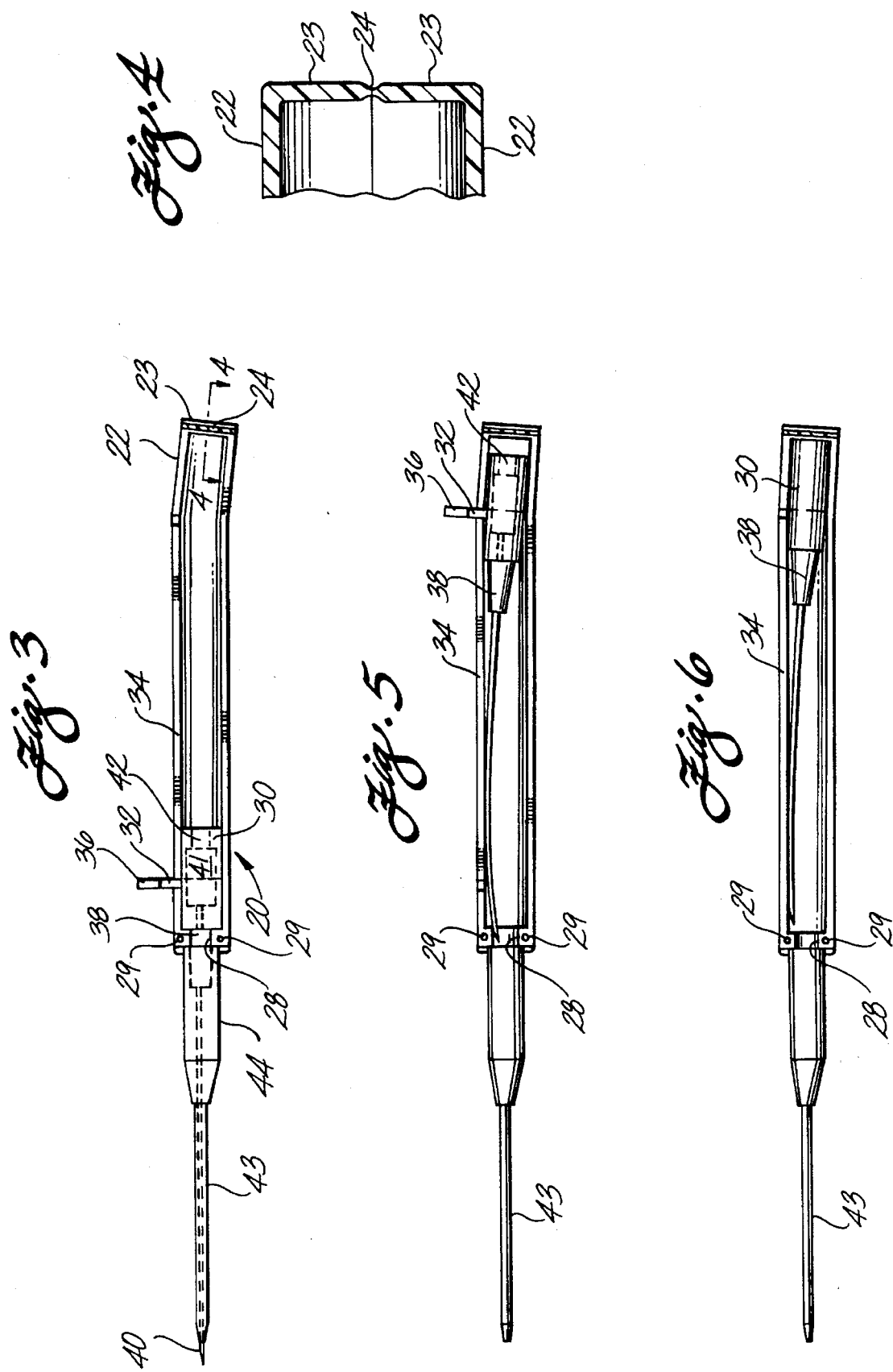

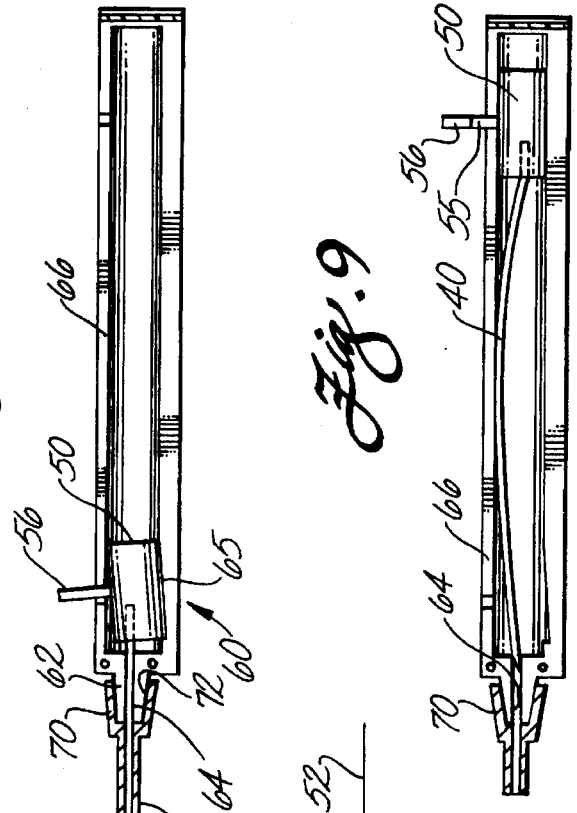

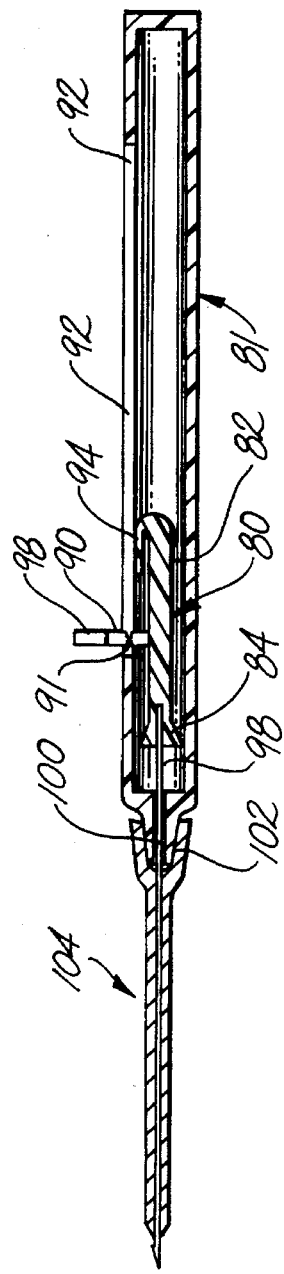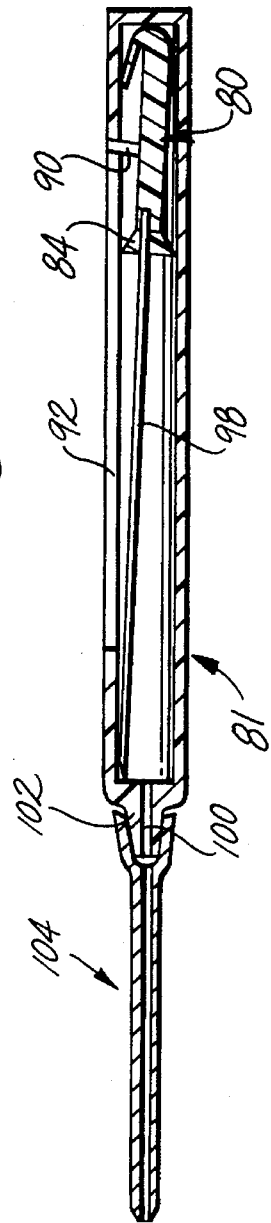

5,456,668

RETRACTABLE VENIPUNCTURE CATHETER NEEDLE AND RECEPTACLE

BACKGROUND OF THE INVENTION

This invention relates to apparatus for intravenous insertion of a catheter.

A catheter is an elongated, resilient, small-diameter tube normally inserted into a vein for the introduction or withdrawal of fluid. The catheter is normally left in position for at least several hours and should be inserted in a way to cause minimum discomfort to the patient.

Typically, a cannula or hollow needle, such as a hypodermic needle made of stainless steel, is disposed within the catheter to provide a sharp point projecting slightly beyond the end of the catheter to be inserted into the vein of the patient. The sharp point of the needle penetrates the skin and vein of the patient with minimum injury and discomfort, and guides the catheter into the vein. Once the catheter is in position, the needle is withdrawn and discarded. Accidental scratching or puncturing of personnel with a used needle can present a serious health hazard, including the possibility of transmitting infectious diseases, such as hepatitis, AIDS, herpes, and the like, from a contaminated used needle.

Many prior art devices have been designed to prevent needle stick from used hypodermic needles. Examples are U.S. Pat. No. 5,256,156 to Marks (1993); U.S. Pat. No. 5,205,829 to Lituchy (1993); U.S. Pat. No. 5,102,394 to Lasaitis et al (1992); U.S. Pat. No. 4,950,252 to Luther et al (1990); U.S. Pat. No. 4,909,793 to Vining et al (1990); and U.S. Pat. No. 5,273,540 to Luther (1993).

The prior art devices have various disadvantages. They have a complicated structure, are not easily operated with one hand, do not provide positive prevention of reuse, or do not provide permanent shielding of the used needle.

SUMMARY OF THE INVENTION

This invention provides intravenous catheter insertion apparatus which is simple, inexpensive, easy to make, and easy to operate with one hand. After the hypodermic needle has been used to insert the catheter, the needle can be positively and permanently enclosed in the housing with one hand and without being exposed so that it cannot be reused or accidentally stick someone. One-handed operation of the apparatus of this invention is important because it leaves the other hand free to stabilize the position of the inserted catheter as the needle is withdrawn to the enclosed position without ever exposing the sharp point of the used needle.

Briefly, the apparatus of this invention includes a carrier disposed in an elongated housing. The carrier is movable by operation with only one hand from a first to a second position by means which extend from the carrier through a longitudinally extending slot in a wall of the housing. An elongated hypodermic needle is secured at one end to the carrier and extends through an opening in the housing so the other (sharp) end of the needle extends from the housing when the carrier is in the first position. The means provided for moving the carrier from the first to the second position permit one-handed operation to retract the needle into the housing until the sharp end of the needle is clear of the opening. Means are also provided for deflecting the needle laterally when the needle is clear of the opening so the needle moves out of alignment with the opening to prevent the needle from being moved by the carrier back into the opening.

The preferred embodiment of the invention includes means for holding the needle in the deflected position. The preferred means for moving the carrier includes a shank which extends from the carrier through the elongated slot in the housing. A tab on the shank exterior of the housing further facilitates sliding the carrier from the first to the second position. Preferably, the shank is of a material and dimension so that it can easily be broken when the carrier is in the second position so the carrier cannot inadvertently be urged back toward the first position.

One of the preferred embodiments for deflecting the needle laterally includes means for rotating the carrier about an axis transverse to the longitudinal axis of the needle as the carrier moves toward the second position. Preferably, the carrier rotates before the needle clears the opening. This deflects the needle into a curved condition, but well within its elastic limit. Thereafter, further movement of the carrier to the second position causes the needle to clear the opening and spring to its normal straight, relaxed condition so that it is no longer aligned with the opening in the housing. Thus, even if the carrier is inadvertently subjected to a force which tends to move the carrier back toward the first position, the sharp end of the needle will jam against the interior of the housing so the needle cannot be re-exposed.

In one preferred embodiment of the invention, the carrier is rotated as it moves by a portion of the housing interior which causes the carrier to follow a nonlinear path as it moves into the second position. In another form, the carrier is spring-loaded to tend it to cause it to rotate about an axis normal to the direction traveled by the carrier and moving from the first to the second position. Rotation of the carrier is resisted by the needle disposed in the housing opening. As the needle clears the opening, the springing means rotates the carrier so the longitudinal axis of the needle is no longer aligned with the opening.

In another embodiment of the invention, the needle and carrier are mounted together so that when the carrier and needle are in the first position, a lateral force is exerted on the needle to subject it to a bending movement and deflect it laterally relative to the carrier, which is prevented from moving laterally by being confined within the housing. As the carrier moves from the first to the second position, the needle clears the housing opening, which releases the lateral force on the needle. This permits the needle to spring to a relaxed position with the longitudinal axis of the needle out of alignment with the opening so that the needle is trapped in the housing.

For simplicity of construction and assembly, the housing is preferably made of two elongated semicylindrical sections molded from a suitable plastic, such as polyethylene, polypropylene, or the like. Preferably, the two sections are joined together at one end by a "living hinge" molded integrally with each of the two sections so they can readily be spread apart or fitted together around the carrier and the needle to form an enclosed housing with an opening at one end remote from the living hinge.

BRIEF DESCRIPTION OF THE DRAWINGS

The invention will be more fully understood from the following detailed description and the accompanying drawings in which:

FIG. 1 is a perspective view of an unassembled embodiment of the invention;

FIG. 2 is a perspective view of the elements of FIG. 1 assembled for use with a catheter (not shown in FIG. 2);

FIG. 3 is a longitudinal sectional elevation taken on line 3—3 of FIG. 2 with a catheter mounted over the needle;

FIG. 4 is a view taken on line 4—4 of FIG. 3;

FIG. 5 is a longitudinal sectional elevation of the apparatus of FIG. 3 with the carrier moved almost to the second position just before the needle clears the opening in the housing;

FIG. 6 is a view similar to FIG. 5 showing the carrier in the second position with the needle locked safely in the housing, and with the tab broken off the carrier;

FIG. 7 is a sectional elevation of a needle mounted in a cylindrical carrier so that the longitudinal axis of the needle is at an angle to the longitudinal axis of the carrier;

FIG. 8 is a sectional elevation of the carrier and needle of FIG. 7 mounted in a housing so that the needle is deflected laterally to make the longitudinal axis of the needle collinear with that of the carrier;

FIG. 9 is a longitudinal sectional elevation of the apparatus of FIG. 8 showing the carrier moved almost to the second position just before the needle clears the opening in the housing;

FIG. 10 is a view similar to that of FIG. 9, except the carrier is in the second position with the needle trapped in the housing, and the tab for moving the carrier is broken off, and the housing has been removed from the catheter;

FIG. 11 is an elongated sectional view showing a leaf spring integrally formed with the carrier for urging the carrier and needle toward a position out of alignment with the opening in the housing; and FIG. 12 is a view similar to FIG. 11 showing the carrier moved to the second position so the carrier is rotated by the leaf spring to move the needle out of alignment with the housing opening.

DETAILED DESCRIPTION OF THE PREFERRED EMBODIMENTS

Referring to FIGS. 1–6, an elongated housing 20 in the shape of a hollow right cylinder is formed from two elongated semicylindrical shells 22 (FIG. 1) and molded from a suitable plastic, such as polytetrafluoride, polyethylene, or polypropylene. The right (as viewed in FIGS. 1–6) end of each semicylindrical shell is molded integrally to a respective transverse semicircular plate 23 (see FIGS. 3 and 4). The straight inner edges of the semicircular plates 23 are joined together by an elongated thin web 24 molded integrally at a respective edge to a respective inner edge of a semicircular plate. The web 24 forms a "living hinge", which permits the shells to be moved like a clam shell from the open position shown in FIG. 1 to the closed position shown in FIG. 2. This facilitates manufacture and assembly of the apparatus.

The left (as viewed in FIGS. 1–6) end of each semicylindrical shell includes a respective transverse semiannular partition 26 molded integrally at its outer edge with the left end of a respective shell so that when the shells are brought together to form the housing as shown in FIG. 2, a circular opening 28 is formed at the left end of the housing.

A carrier 30 in the form of a right cylinder makes a sliding fit within the housing. The carrier is also preferably molded from a suitable plastic, such as polytetrafluoride, polyethylene, or polypropylene. A vertical shank 32 is molded integrally at its lower with the upper (as viewed in FIGS. 1–6) portion of the central part of the carrier, and extends up through a longitudinal slot 34 formed between upper adjacent edges of the two shells of the housing. A transverse tab 36 is molded integrally with the upper end of the shank. Thus, the carrier can be moved from a first position where the shank is at the left end of the slot to a second position where the shank is at the right end of the slot.

An elongated frustoconical nose 38 is formed integrally at the left end of the carrier to taper inwardly away from the carrier and extend through the opening 28 at the left end of the housing. An elongated cannula or hypodermic needle 40 has its right (as viewed in FIGS. 1–6) end embedded in the nose of the carrier so the longitudinal axis of the needle is coaxial with the longitudinal axes of the carrier and the housing. The right end of the needle opens into a cavity 41 in the carrier. The cavity receives the flow of blood resulting from the insertion of the needle into the vein of a patient. A venting filter 42 fitted in the right end of the carrier vents air from the cavity and prevents flow of blood from the cavity. The plastic carrier and housing are sufficiently transparent to permit observation of the blood entering the cavity ("flash back"), and thus confirm that the catheter is properly located in a vein.

As shown in FIG. 3, a catheter 43, which may be of conventional construction, fits over the hypodermic needle so that the sharp point on the needle projects just beyond the left end of the catheter. The right end of the catheter carries a conventional tapered socket 44 which makes a snug friction fit over the nose of the carrier.

As shown in FIG. 1, one of the semiannular partitions 26 carries a pair of transverse pins 45, each of which makes a snug snap fit in a corresponding recess 46 in the other semicircular plate to hold the shells together in the assembled portion shown in FIGS. 2–6. If desired, the adjacent edges of the two shells are provided with a tongue and groove fit (not shown) to increase the fastening force between the two shells. Alternatively, the two shells are bonded together, such as with an adhesive or by heat fusion of the plastic material which forms them.

As shown best in FIGS. 3, 5, and 6, the right end of the housing is offset slightly from the remainder of the housing so that the longitudinal axis of the right end portion of the housing is at an angle of between about 2 and about 5 degrees with respect to the longitudinal axis of the remainder of the housing.

With the catheter assembled on the hypodermic needle, as shown in FIG. 3, the needle and catheter are inserted in the vein of a patient in the usual manner. After the catheter is properly located, the administering person holds the inserted catheter in place with one hand, and uses the other hand to withdraw the needle from the catheter and into the housing by simply holding the housing in one hand and sliding the tab 36 from left to right so that the carrier moves from a first position (shown in FIG. 3) toward a second position at the right end of the housing. As the carrier moves from left to right, the carrier enters the offset portion at the right end of the housing. The clearance between the carrier and the housing interior is sufficient to permit the carrier to rotate in a clockwise direction (as viewed in FIG. 5) about an axis perpendicular to the longitudinal axis of the housing and the needle. As shown in FIG. 5, as the left end of the hypodermic needle with the sharp point enters the opening 28, the carrier rotates slightly and subjects the needle to a slight bending moment which causes the needle to bow upwardly, but not in an amount which exceeds the elastic limit of the material of which the needle is made. Normally, the hypodermic needle will be stainless steel and be between about 16 gauge to about 24 gauge, depending on the size of the patient.

As the tab 36 moves farther to the right so that the shank is against the right end of the slot 34, the left end of the needle clears the opening and springs upwardly to the position shown in FIG. 6 so that the needle is no longer aligned with the longitudinal axis of the housing passing through the hold, and cannot be moved back through the hole to the exterior of the housing. A further force on the tab to the right (as viewed in FIG. 6) causes the shank to break so the tab can be removed, and no force can be inadvertently applied to the carrier to urge it away from the retracted (second) position shown in FIG. 6.

The one-handed operation of the device leaves one hand free to hold the catheter in the desired position, while the other hand withdraws the needle and safely encloses it in the housing without ever exposing the sharp end of the used needle. Thus, the used needle cannot be inadvertently reused or cause injury or infection to personnel.

Referring to FIG. 7, an elongated carrier 50 cast of plastic in the shape of a right cylinder has a longitudinal axis 52. An elongated straight hypodermic needle or cannula 54 is embedded in one end of the carrier so that the sharp end of the needle extends away from the carrier at an angle of between about 2 to about 5 degrees from the longitudinal axis of the carrier, which has an upwardly extending shank 55 and tab 56. The right (as viewed in FIG. 7) end of the needle opens into a cavity 57 connected to a venting filter 58 so that "flash back" can be observed, as described above with respect to FIGS. 1–6.

FIG. 8 shows the carrier 50 mounted in a housing 60 almost identical with the housing 20 of FIGS. 1–6, except that the right (as viewed in FIGS. 8–10) end of the housing is straight, that is, not offset from the central part of the interior of the housing, so that the right end and central part of the housing interior is in the form of a hollow right cylinder. The lower portion of the left end (as viewed in FIGS. 8–10) of the housing interior includes an offset section 65 which slopes outwardly and toward the left to provide an enlarged space for the left end of the carrier 50, which extends downwardly to the left to accommodate the angle between the longitudinal axes of the needle and the carrier when the carrier is at the left end of the housing.

An external nose 62 is formed integrally with the left end of the housing to taper inwardly away from the housing. An elongated opening 64 extends longitudinally through the center of the nose to make a close fit around the needle 54 so the longitudinal axis of the needle is collinear with the longitudinal axis of the housing.

Although not shown in FIGS. 8–10, the housing 60 is also made of two semicylindrical shells, as described above with respect to FIGS. 1–6, and the nose 62 at the left end of the housing 60 is formed of two separate cylindrical pieces, each integrally molded with a respective shell. When the shells of housing 60 are snapped together, as described above with respect to the housing shown in FIGS. 1–6, the housing 60 makes a close sliding fit around the inclined carrier 50 in the enlarged space at the left end of the housing, and the opening 64 in the nose 62 makes a close fit around the needle 40. Thus, the needle is in the extended position shown in FIG. 8, that is, with the carrier in the first position.

The carrier shank 55 extends up through an elongated slot 66 formed in the upper (as viewed in FIGS. 8–10) portion of the housing so that the tab 56 can be moved with one hand from the first position, shown in FIG. 8, to the second position, shown in FIG. 10.

An elongated catheter 68, fitted over the hypodermic needle, carries a fitting 70 with a tapered socket 72 which makes a snug friction fit with the exterior surface of the nose 62 on the housing. The left end of the catheter stops just short of the exposed and sharpened end 74 of the hypodermic needle.

After the needle and catheter have been inserted in the usual manner, the needle is withdrawn with one hand by sliding the tab from the first position shown in FIG. 8 toward the second position at the right (as viewed in FIGS. 8–10) end of the housing. As the carrier and needle slide to the right, the carrier moves up the slope of offset section 65 and rotates in a clockwise (as viewed in FIGS. 8–10) until the longitudinal axes of the carrier and housing are collinear to impose on the needle a slight bending movement which does not exceed the elastic limit of the needle material. As the needle reaches the inner end of the opening 64, the bending moment imposed on the needle by the misalignment of the normal (i.e., unstressed) longitudinal axis of the needle with the longitudinal axes of the carrier and housing causes the needle to curve concave upwardly, as shown in FIG. 9.

As the carrier and needle move farther to the right to the fully retracted or second position, the left end of the needle clears the opening 64 and snaps up to the position shown in FIG. 10 so that the needle is no longer in alignment with the opening 64, and cannot be moved either accidentally or deliberately back to the exposed position.

As with the tab of the embodiment shown in FIGS. 1–6, the tab on the carrier shown in FIGS. 7–9 is designed so that it can easily be snapped off, as shown in FIG. 10, by the use of only one hand.

FIGS. 11 and 12 show another embodiment of the invention in which a carrier 80 in a housing 81 includes an elongated right cylindrical body 82 with a frustoconical head 84 formed integrally with the left (as viewed in FIGS. 11 and 12) end of the body. The head tapers outwardly toward the left. The maximum diameter of the head is greater than the rest of the carrier, but slightly less than the internal diameter of the housing so the head and carrier can rotate about an axis perpendicular to the longitudinal axis of the housing and the carrier.

The housing 81, identical with the housing shown in FIGS. 8–10, surrounds the carrier, which has a tab 88 on the upper end of an upwardly extending shank 90 formed integrally with the carrier. The shank extends up through a longitudinally extending slot 92 in the upper part of the housing so the tab and carrier can be moved relative to the housing with on hand, as described above.

An intermediate part 91 of the shank (in the vicinity of the slot 92) is of reduced cross section so the tab can be easily snapped off at that point with one-handed operation.

An elongated leaf spring 94 is formed integrally with the right (as viewed in FIGS. 11 and 12) end of the carrier and curves upwardly and to the left over the right end of the carrier. The leaf spring bears against the upper surface of the housing interior to urge the carrier to pivot in a clockwise direction (as viewed in FIGS. 10 and 11) about the point of contact between the lower portion of the head 84 and the lower interior surface of the housing. An elongated hypodermic needle or cannula 98 has one end embedded in the left (as viewed in FIGS. 11 and 12) end of the carrier to be collinear with the longitudinal axis of the carrier and to extend out through a close fitting opening 100 in a tapered nose 102 integrally formed with the left (as viewed in FIGS. 11 and 12) end of the housing. A conventional catheter 104, fits over the needle as described above for FIGS. 8–10.

FIGS. 11 and 12 do not show the cavity and venting filter in the carrier 80 for observing flash back.

After the needle and catheter are inserted in the conventional manner, the needle is withdrawn into the housing by moving tab 88 to the right (as viewed in FIGS. 11 and 12) until the shank 90 comes to a stop against the right (as viewed in FIG. 11) end of slot 92. As the tab 90 moves from right to left, it moves the carrier and needle from the first (extended) position shown in FIG. 11 to the second (retracted) position shown in FIG. 12. As the needle moves to the right, and the sharp point at the left end of the needle clears the inner end of the opening 100, and the leaf spring 94 forces the right end of the carrier down so the carrier rotates slightly in a clockwise direction (as viewed in FIG. 12) about an axis perpendicular to the longitudinal axis of the carrier, housing, and needle. This moves the left end of the needle up to the position shown in FIG. 12 so that the needle is no longer aligned with the opening 100. by the action of The leaf spring 94 holds the needle in the misaligned position. Further movement of the tab to the right causes the shank to break where it is of reduced cross-sectional area. Thereafter, the needle cannot again be extended from the housing.

In each of the foregoing embodiments, the housing is substantially rigid from one end to the other so the needle is subjected to the required bending movement to cause the needle to move to, and be retained in, the captured position as the needle is drawn into the housing.

Each of the embodiments described above can easily be operated with one hand by either holding the housing between the thumb and middle finger, and using the index finger to retract the tab. Alternatively, the housing can be grasped in the palm of the hand with four fingers, and the tab retracted by sliding it back with the thumb. In either case, the other hand is free to hold the catheter in place as the sharp needle is retracted and safely stored in the housing. Thereafter, the housing nose is disengaged from the catheter so the sharp end of the used needle is never exposed where it could cause injury or infection.

Although not shown in the drawings, the nose 38 of the embodiment shown in FIGS. 1–6 can be replaced by the nose 62 arrangement of the embodiments shown in FIGS. 7–12, and vice versa. However, the nose 62 arrangement is presently preferred because it presents a smaller opening around the needle, which ensures a more secure capture of the used needle, and because the catheter can stay connected to the housing until the needle is completely withdrawn into the housing.

I claim:

1. Intravenous catheter apparatus comprising:

an elongated housing having a longitudinally extending slot opening from the housing interior to the exterior;

a carrier in the housing, the carrier being movable from a first to a second position in the housing;

means extending from the carrier through the slot to facilitate one-handed operation for moving the carrier from the first to the second position;

an elongated needle secured at one end to the carrier, the needle extending from the carrier and through an opening in the housing so the other end of the needle extends from the housing when the carrier is in the first position; and means for moving the carrier from the first to the second position to retract the needle into the housing until the said other end of the needle is clear of the opening, the housing interior being shaped to have a first longitudinal axis at the first position and a second longitudinal axis at the second position, the first and second axes being angled relative to each other so as the carrier moves from the first to the second position it deflects the needle laterally when the needle is clear of the opening so the needle moves out of alignment with the opening to prevent the needle from being moved by the carrier back into the opening.

2. Apparatus according to claim 1 in which the means for moving the carrier includes a tab secured to the carrier by a shank extending through the longitudinal slot in the carrier.

3. Apparatus according to claim 2 in which the shank is breakable by manual operation.

4. Apparatus according to claim 1 in which the carrier rotates before the needle clears the opening so as to impart a bending force on the needle.

5. Apparatus according to claim 4 in which the needle is withdrawn into the housing and clear of the opening without exceeding the elastic limit of the needle.

6. Apparatus according to claim 1 in which the needle extends from the carrier at an angle relative to the direction in which the carrier moves as the carrier leaves the first position.

7. Apparatus according to claim 1 in which the housing is formed from two mating elongated shells.

8. Apparatus according to claim 7 in which the elongated shells are secured together at one end by a hinge.

9. Apparatus according to claim 7 or 8 which includes mating means for holding the shells together to form the housing.

10. Intravenous catheter apparatus comprising:

an elongated housing having a longitudinally extending slot opening from the housing interior to the exterior;

a carrier in the housing, the carrier being movable from a first to a second position in the housing;

a shank secured to and extending from the carrier through the slot and away from the housing to facilitate one-handed operation for moving the carrier from the first to the second position; and an elongated needle secured at one end to the carrier, the needle extending from the carrier and through an opening in the housing so the other end of the needle extends from the housing when the carrier is in the first position, the slot being sufficiently long so the shank can be used to move the carrier from the first to the second position to retract the needle into the housing until the said other end of the needle is clear of the opening, the shank being breakable by manual operation when the carrier is in the second position.

11. Apparatus according to claim 10 in which an intermediate part of the shank in the vicinity of the slot is of reduced cross section to facilitate breaking the shank by manual operation.

12. Apparatus according to claim 10 or 11 which includes a tab secured to the shank outside the housing to facilitate moving the shank and breaking it by manual operation when the carrier is in the second position.

13. Intravenous catheter apparatus comprising:

an elongated housing having a longitudinally extending slot opening from the housing interior to the exterior;

a carrier in the housing, the carrier being movable from a first to a second position in the housing;

means extending from the carrier through the slot to facilitate one-handed operation for moving the carrier from the first to the second position;

means for moving the carrier from the first to the second position to retract the needle into the housing until the said other end of the needle is clear of the opening; and a leaf spring secured to the carrier to act laterally against the interior of the housing for rotating the carrier relative to the housing about an axis transverse to the longitudinal axis of the needle after the needle is withdrawn into the housing so the needle moves out of alignment with the opening to prevent the needle from being moved by the carrier back into the opening.

* * * * *